United States Patent [19]
Sciullo et al.

[11] Patent Number: 5,632,297
[45] Date of Patent: May 27, 1997

[54] PISTON-TYPE THERMALLY OR PRESSURE ACTIVATED RELIEF DEVICE

[75] Inventors: Dino V. Sciullo, Pittsburgh; Robin N. Borland, McMurray; James R. Daniels, McDonald, all of Pa.

[73] Assignee: Amcast Industrial Corporation, Dayton, Ohio

[21] Appl. No.: 534,195

[22] Filed: Sep. 26, 1995

Related U.S. Application Data

[63] Continuation-in-part of Ser. No. 373,662, Jan. 17, 1995, Pat. No. 5,511,576.

[51] Int. Cl.⁶ ................................................ F16K 17/38
[52] U.S. Cl. ................................................ 137/73; 137/72
[58] Field of Search ................................. 137/72, 79, 73

[56] References Cited

U.S. PATENT DOCUMENTS

| | | | |
|---|---|---|---|
| 1,636,065 | 7/1927 | Mueller et al. | 137/73 |
| 1,944,518 | 1/1934 | Lovehim et al. | 137/73 |
| 2,194,541 | 3/1940 | Buttner | 137/73 |
| 2,671,461 | 3/1954 | Hebert. | |
| 2,697,915 | 12/1954 | Chisholm | 137/73 |
| 3,040,764 | 6/1962 | Feinberg | 137/73 |
| 3,618,627 | 11/1971 | Wagner | 137/73 |
| 3,896,835 | 7/1975 | Wicke. | |
| 4,221,231 | 9/1980 | Harvey et al.. | |
| 4,365,643 | 12/1982 | Masclet et al.. | |
| 4,503,675 | 3/1985 | Gardner et al.. | |
| 4,553,589 | 11/1985 | Jennings et al.. | |
| 4,744,382 | 5/1988 | Visnic et al.. | |
| 4,744,383 | 5/1988 | Visnic et al.. | |
| 4,800,948 | 1/1989 | Visnic. | |
| 5,197,671 | 5/1993 | Wass et al.. | |
| 5,223,347 | 6/1993 | Lhymn et al.. | |
| 5,255,809 | 10/1993 | Ervin et al.. | |
| 5,400,817 | 3/1995 | Voss et al.. | |

Primary Examiner—John C. Fox
Attorney, Agent, or Firm—Killworth, Gottman, Hagan & Schaeff

[57] ABSTRACT

A relief device which activates in response either to excess temperatures or pressures in or around a pressurized vessel and which resists extrusion related failures even at high pressures is provided. The relief device includes a body having an inlet, an outlet, and a fluid flow passage communicating with the inlet and outlet. The body further includes a fluid escape passage having a member therein which is porous to gases and liquids but not to solids and a plug of a fusible material which melts at a predetermined temperature positioned adjacent to the porous member. A first piston is positioned in the fluid flow passage and is normally biased into a sealing relationship with the inlet. A second piston is positioned in the fluid escape passage and is normally biased against and applies a compressive force on the plug of fusible material.

24 Claims, 5 Drawing Sheets

PISTON-TYPE THERMALLY OR PRESSURE ACTIVATED RELIEF DEVICE

CROSS-REFERENCE TO RELATED APPLICATIONS

This application is a continuation-in-part of U.S. Patent application Ser. No. 08/373,622, filed Jan. 17, 1995, and entitled PISTON-TYPE THERMALLY ACTIVATED RELIEF DEVICE, now U.S. Pat. No. 5,511,576, issued Apr. 30, 1996, the disclosure of which is hereby incorporated by reference.

BACKGROUND OF THE INVENTION

The present invention relates to a relief devices which may be either thermally or pressure activated to relieve pressure in pressurized containers when a predetermined temperature or pressure in or around the container is exceeded.

Most vessels or containers containing a gas or liquid under pressure are equipped with relief valves to prevent catastrophic rupture of the vessels in the case of excessive pressures or temperatures. For example, vehicles using alternative fuels such as compressed natural gas (CNG) require the presence of one or more fuel cylinders on board containing such gas under pressure. Federally mandated regulations require that such cylinders be equipped with relief valving mechanisms which, in the event of a fire, will allow the gas to escape from the cylinder before reaching an unacceptably high pressure. This reduces the potential for an explosion.

Several approaches have been used to produce acceptable thermally activated relief valves. For example, one approach has been to incorporate a fusible plug of a eutectic metal that blocks and seals an outlet passage in the pressure vessel. Once the temperature surrounding the vessel reaches the yield point of the eutectic metal, the plug melts and pressure forces the melted plug material out through the passage to provide a controlled escape path for the gas in the vessel to vent through.

A major problem arises, however, in that essentially all commercially available eutectic metals, when exposed to high pressures, tend to extrude (creep or cold flow) over time and produce a potential gas leak path. For that reason, conventional fusible plug type devices are not recommended for uses in which the eutectic metal alloy is exposed to container pressures in excess of 500 psig. However, compressed natural gas fuel tanks can have pressures of up to 4500 psig, if a 3600 psig nominal working pressure system is subject to a temperature compensated fill to 1.25 times "settled pressure". Standards adopted by the Compressed Gas Association for Type CG-9 pressure relief devices used in CNG powered vehicles require that no visible extrusion of the fusible metal occur after 26,000 cycles between 300 psig and 70% of the fuel tank test pressure when tested at 180° F. and further that no visible extrusion occur after 500 hours of exposure to 70% of the tank test pressure when tested at 180° F.

Several approaches have been used in attempts to meet these stringent standards. Visnic, U.S. Pat. No. 4,800,948 and Visnic et al., U.S. Pat. Nos. 4,744,382 and 4,744,383 all teach thermally activated pressure relief devices which use arduous flow paths to prevent extrusion of the fusible plug material. Wass et al., U.S. Pat. No. 5,197,671, teach a pressure relief valve with a thermal trigger which includes a eutectic metal alloy and which engages a seal plug. When a predetermined temperature is exceeded, the trigger releases the seal plug to open a gas flow path. Ervin et al., U.S. Pat. No. 5,255,809, teach a different approach for a pressure relief device; rather than the use of a fusible plug, Ervin et al. use a memory metal which changes its shape and opens a valve in response to temperature changes.

Such relief devices, which are actuated by a sensed temperature rise, however, have some additional shortcomings. If the pressure of the gas in a cylinder increases beyond safe limits for some reason other than a rise in temperature, or if the temperature rise is isolated at a point removed from the fusible plug and yet causes a pressure rise in the cylinder, a temperature-activated relief device will not be activated in those circumstances. It would be desirable to have a pressure-activated device which is responsive to overpressure in a cylinder for such situations.

Thus, there remains a need in this art for thermally or pressure activated relief devices which will reliably activate to prevent a catastrophic pressure rupture of a pressure vessel and yet not develop an extrusion-related failure due to extrusion of a fusible alloy.

SUMMARY OF THE INVENTION

The present invention meets that need by providing a relief device which activates in response either to excess temperatures or pressures in or around a pressurized vessel and which resists extrusion related failures even at high pressures. The relief device reliably activates to relieve excess pressure in a vessel and prevents catastrophic pressure ruptures of a vessel. In accordance with one aspect of the invention, a thermally or pressure activated relief device is provided and includes a body having an inlet, an outlet, and a fluid flow passage communicating with the inlet and outlet. The body further includes a fluid escape passage having a member therein which is porous to gases and liquids but not to solids; that is, the member will permit the passage of gases and liquids therethrough, but not solid materials. A plug of a fusible material which melts at a predetermined temperature is positioned adjacent to the porous member in the fluid escape passage.

A first piston is positioned in the fluid flow passage, the first piston having first and second ends and being normally biased into a sealing relationship with the inlet. A second piston is positioned in the fluid escape passage, the second piston being normally biased against and applying a compressive force on the plug of fusible material.

In a preferred embodiment of the invention, the first and second pistons are biased by one or more belleville springs which apply a compressive force against the first piston to seal it against the inlet and apply an opposing compressive force against the second piston and fusible plug to seal the fluid escape passage. The use of belleville springs is preferred because of their repeatability in providing proper compressive forces. Alternatively, other conventional biasing mechanisms may be used in place of the belleville spring(s) such as, for example, a coiled spring. The relief device also includes a mechanism for adjusting the biasing forces on the first and second pistons so that the device can be adjusted to open in response to a predetermined pressure. Such an adjustment mechanism may be, for example, a threaded nut positioned in the fluid escape passage which can be turned to increase or decrease the compressive forces on the pistons. Such a threaded nut includes a flow passage therethrough to permit fluid escape.

The first end of the first piston preferably includes a seat which receives a gasket which seals against the inlet. The first and second pistons are preferably assembled together such that the second end of the first piston is slidably received in an annular opening in the second piston.

The porous member is preferably comprised of a material which provides a tortuous flow path or paths for a fluid (liquid or gas). In a preferred embodiment of the invention, the porous member is comprised of a sintered metal such as bronze. The sintered member may be fabricated by compressing together multiple small spheres of metal and sintering them together into a unitary member, with the spaces between the spheres providing multiple flow paths. Such a material resists extrusion of the solid fusible material therethrough.

The thermally or pressure activated relief device of the present invention may be used as a stand-alone device which is adaptable to be mounted into any opening in a pressurized vessel. The device operates to release gas from the pressurized vessel when the temperature adjacent the vessel exceeds a predetermined threshold or when the pressure in the vessel exceeds a predetermined threshold.

Further, the relief device can readily be adapted to be integrated into a bidirectional valve for controlling the flow of a compressed gas to and from a pressurized vessel such as a compressed natural gas-containing fuel cylinder for a CNG powered vehicle. In this embodiment, the relief device functions to prevent the fuel cylinder from rupturing by relieving excessive gas pressure in the cylinder, such as in the event of a fire or an over-filling of the fuel cylinder.

In operation, the fusible alloy plug is compressed between the second piston and the porous member in the fluid escape passage. If the temperature exceeds a predetermined threshold, the plug material will melt and, due to the compressive force exerted by the second piston, will flow through the porous member and out through the escape passage. As the plug material flows, the second piston moves into the space previously occupied by the plug member. This movement of the second piston permits the gas pressure in the cylinder to unseat the seal over the inlet to the cylinder and start the flow of gas through the outlet, thus relieving any pressure buildup. Alternatively, if the gas pressure in the cylinder exceeds a predetermined threshold, but without an accompanying temperature rise sufficient to melt the fusible alloy plug, the biasing force of the spring will be overcome and the first piston will move upwardly into the annular opening in the second piston. Again, the gas pressure in the cylinder will cause movement of the piston to unseat the seal over the inlet to the cylinder and start the flow of gas through the outlet.

Accordingly, it is a feature of the present invention to provide a temperature and pressure activated relief device which resists extrusion related failures even at high pressures and yet reliably activates to relieve pressure buildups in a vessel and prevents catastrophic pressure ruptures of vessels. This, and other features and advantages of the present invention, will become apparent from the following detailed description, the accompanying drawings, and the appended claims.

DETAILED DESCRIPTION OF THE PREFERRED EMBODIMENTS

Figure 1:
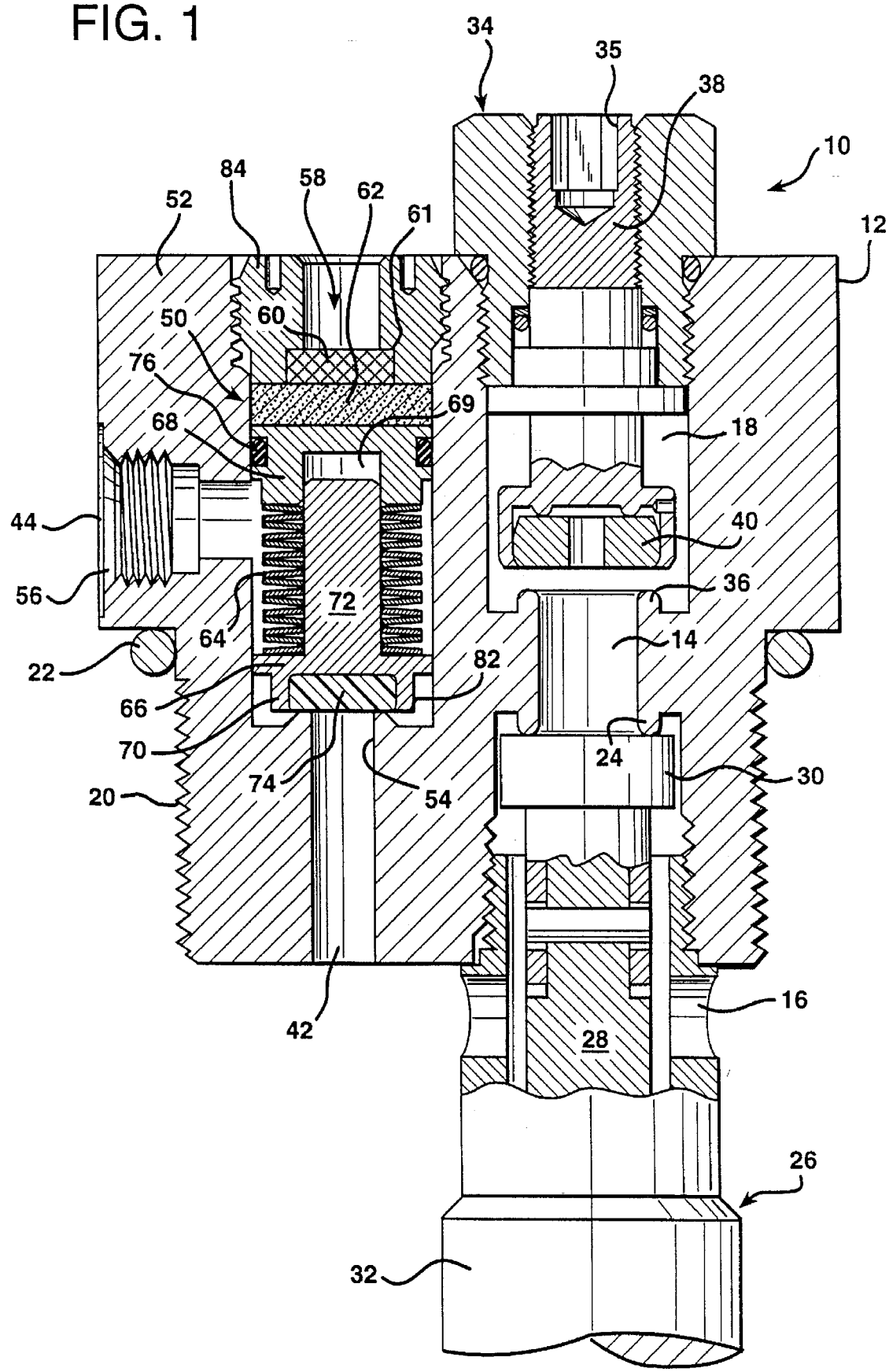
FIG. 1 is a side view, partially in cross-section, of the temperature and pressure relief device of the present invention configured with a bidirectional solenoid-actuated valve.

While it will be apparent to those skilled in the art that the thermally and pressure activated relief device of the present invention may be adapted for use with essentially any pressure vessel where there is a need for pressure relief, including both gas and liquid-filled vessels, the invention will be explained in terms of several preferred embodiments of the invention. One of those embodiments is illustrated in FIG. 1 which shows a bidirectional valve 10 which includes a valve body 12 which has a first gas flow passage 14 which extends through the valve body from a first end 16 which communicates with the interior of a pressurized vessel (not shown) to a second end 18 which communicates with outlet ports (not shown) on the valve body. Valve body 12 includes external threads 20 which permit the valve to be screwed into a corresponding set of threads on a neck of a pressurized vessel. A resilient O-ring 22 provides for sealing between valve body 12 and pressurized vessel. Valve 10, and its component parts, may be fabricated of brass, steel, stainless steel, or aluminum, and may include plating or other surface treatment to resist corrosion.

In gas flow passage 14 is valve seat 24. Also positioned in gas flow passage 14 is solenoid valve 26 which includes a plunger 28, poppet head 30, and housing 32. Plunger 28 and poppet head 30 are slidable in gas flow passage 14. A spring (not shown) normally biases poppet head 30 into a sealing relationship with valve seat 24. A solenoid coil (not shown), when actuated, causes plunger 28 to move away from popper head 30, thereby permitting the valve seat to open as is explained in greater detail in commonly-assigned U.S. Patent application Ser. No. 08/200,075, filed Feb. 22, 1994, now U.S. Pat. No. 5,452,738, issued Sep. 26, 1995, the disclosure of which is incorporated by reference herein.

Referring again to FIG. 1, bidirectional valve 10 also includes an optional manual lockdown valve 34 which is positioned in gas flow passage 14 between valve seat 24 and the second end 18 of the flow passage. Manual lockdown valve 34 permits pressure testing of the valve and fuel supply system to insure that they are leak tight under a range of normal operating pressures of up to about 3600 psi. Manual lockdown valve 34 can be tightened using a tool such as an Allen wrench (not shown) in socket 35 to seal against a second valve seat 36 in gas flow passage 14. As shown, the threaded stem 38 may be rotated to tighten resilient gasket 40 against valve seat 36 to seal gas flow passage 14.

Still referring to FIG. 1, valve body 12 also includes a second gas flow passage 42 which communicates at one end with the interior of the pressurized vessel and at the other end communicates with a gas vent port 44 on the valve body. The thermally and pressure activated relief device, generally indicated at 50, of the present invention is mounted in second gas flow passage 42. Relief device 50 includes a body 52 having an inlet 54 and an outlet 56. Second gas flow passage 42 communicates between inlet 54 and outlet 56. Body 52 may be made from any suitable metal such as, for example, brass.

Body 52 includes a fluid escape passage 58 which permits the fusible material to escape under conditions as explained in greater detail below. Blocking fluid escape passage 58 is member 60 which is porous to gases and liquids, but not solids. As shown, member 60 may be seated in a cut-out shoulder area 61 in threaded nut 84. Preferably, member 60 is comprised of a sintered metal such as bronze. The sintered bronze may take the form of multiple small diameter spheres which have been sintered together to form a single body. The spaces between the spheres form numerous fluid flow passages, but resist the passage of solids because of the small area of the passages and their many changes in direction. It will be appreciated by those skilled in the art that member 60 may take a number of forms and can be made of any material which has the characteristics of being porous to gases and liquids, but which is not porous to solids, and which includes numerous small flow passages, preferably providing tortuous flow paths.

As shown in FIG. 1, thermally activated relief device 50 also includes a plug 62 of a fusible material, preferably a fusible metal eutectic alloy having a melting point of 217° F. Such fusible alloys and their melting points are well known in the art. Different eutectic alloys may be chosen depending on the desired temperature at which the relief device is designed to open. Plug 62 is positioned adjacent porous member 60 and out of the second gas flow passage 42. Plug 62 is held in place adjacent member 60 by the compressive forces of a stacked series of belleville springs 64 which act simultaneously on a first piston 66 positioned in gas flow passage 42 and a second piston 68. The pistons are preferably made of stainless steel.

First piston 66 has a first end 70 and a second end 72. First end 70 includes a recessed area which holds a resilient gasket 74 of a sealable elastomeric material, such as for example a polyamide (Vespel® from DuPont), which seals against inlet 54. As shown, gasket 74 seals a smaller surface area than the surface area of the face of second piston 68 abutting fusible plug 62. By manufacturing the pistons and gasket in this manner, the force acting on fusible plug 62 is reduced to lessen any tendency of the plug alloy to extrude through creep or cold flow. Thus, if the area sealed by gasket 74 has a diameter D1, and the face of second piston 68 has a diameter D2, and D1<D2, then the compressive stress placed on plug 62 will be equal to the vessel pressure multiplied by $\pi/4 \times (D1/D2)^2$. Thus, the design of the relief device of the present invention acts to minimize any possible extrusion-related failures by the fusible alloy by positioning fusible plug 62 outside of gas flow passage 42, by including porous member 60 with tortuous flow passages, and by designing the pistons and gasket seals to reduce compressive loading on the fusible plug.

As also shown in FIG. 1, second piston 68 includes an O-ring 76 to seal against the sides of fluid escape passage 58 and prevent any gas from the pressurized vessel from leaking out through that passage. Preferably, O-ring 76 in manufactured of a nitrile rubber such as Viton® or other suitable resilient material designed for high temperature operation. The compressive force applied by belleville springs 64 against plug 62 insure that in the event that the temperature exceeds the melting point of the fusible alloy, the melted material will be forced through passage 58. Second piston 68 also includes an annular opening 69 into which the second end 72 of first piston 66 is slidably received.

Figure 3:
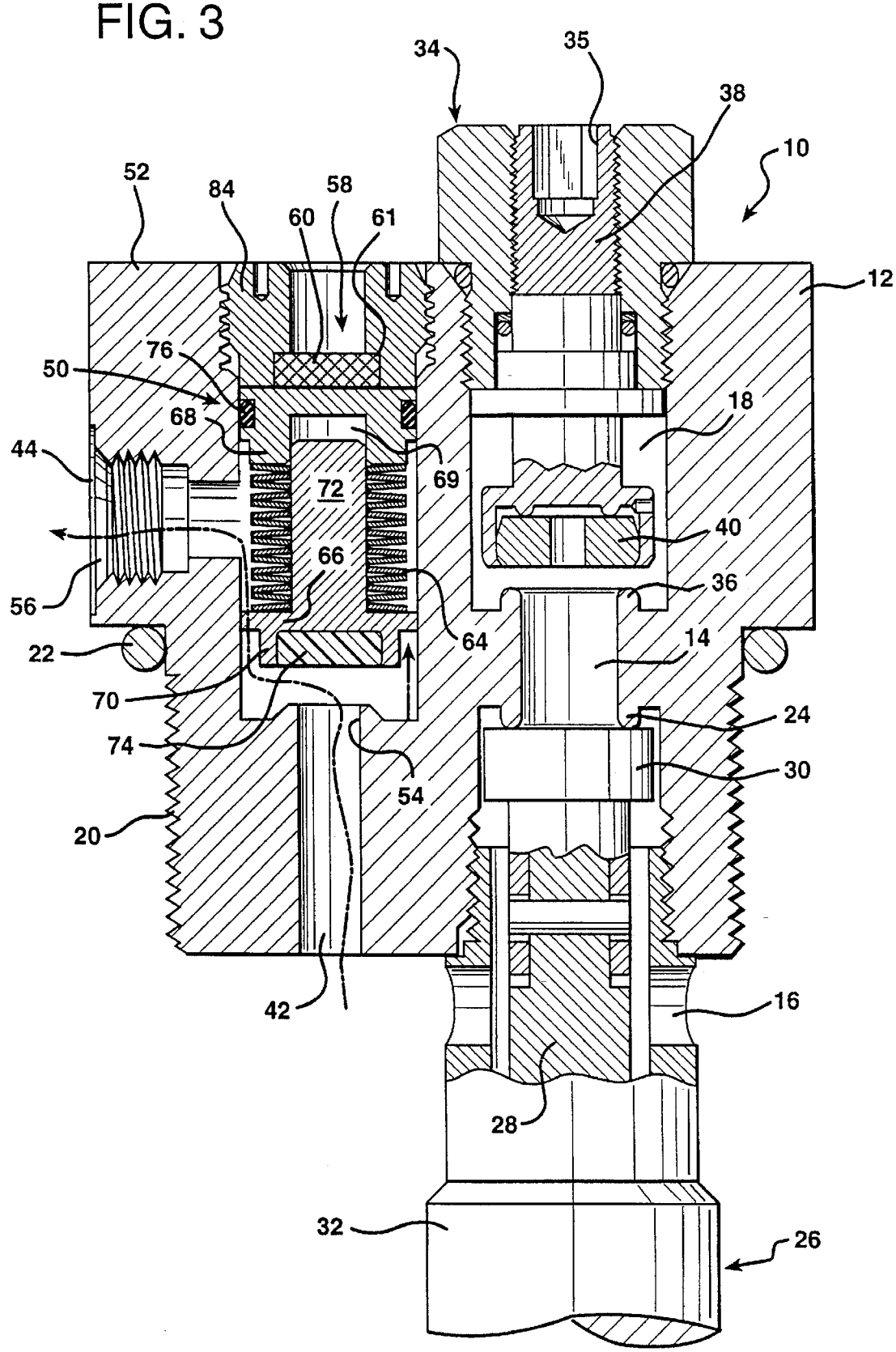
FIG. 3 is a side view, partially in cross-section, of the relief device after thermal activation in which the fusible metal alloy plug has melted and the pistons have been displaced into the space formerly occupied by the plug.

During normal operation of bidirectional valve 10, relief device 50 maintains a gas tight seal. If, however, the temperature adjacent the valve body or pressurized vessel rises above a predetermined limit, such as in the event of a fire, the heat from the fire will transfer to fusible plug 62 causing it to melt and flow through porous member 60 and out escape passage 58 (aided by the force of belleville springs 64 against second piston 68). As best shown in FIG. 3, where like reference numerals represent like elements, the combination of the compressive force on belleville springs 64 acting on second piston 68 and the force due to gas pressure in the vessel acting on the area sealed by gasket 74 causes the piston and spring assembly to move upwardly into the space vacated by the fusible alloy material. Activation time for the relief device is quick. This movement opens inlet 54 and gas flow passage 42 and permits the pressurized gas in the vessel to vent to the exterior through port 44 as depicted by the arrow. As this gas escapes, the pressure in the vessel will reduce, avoiding catastrophic rupture.

Figure 4:
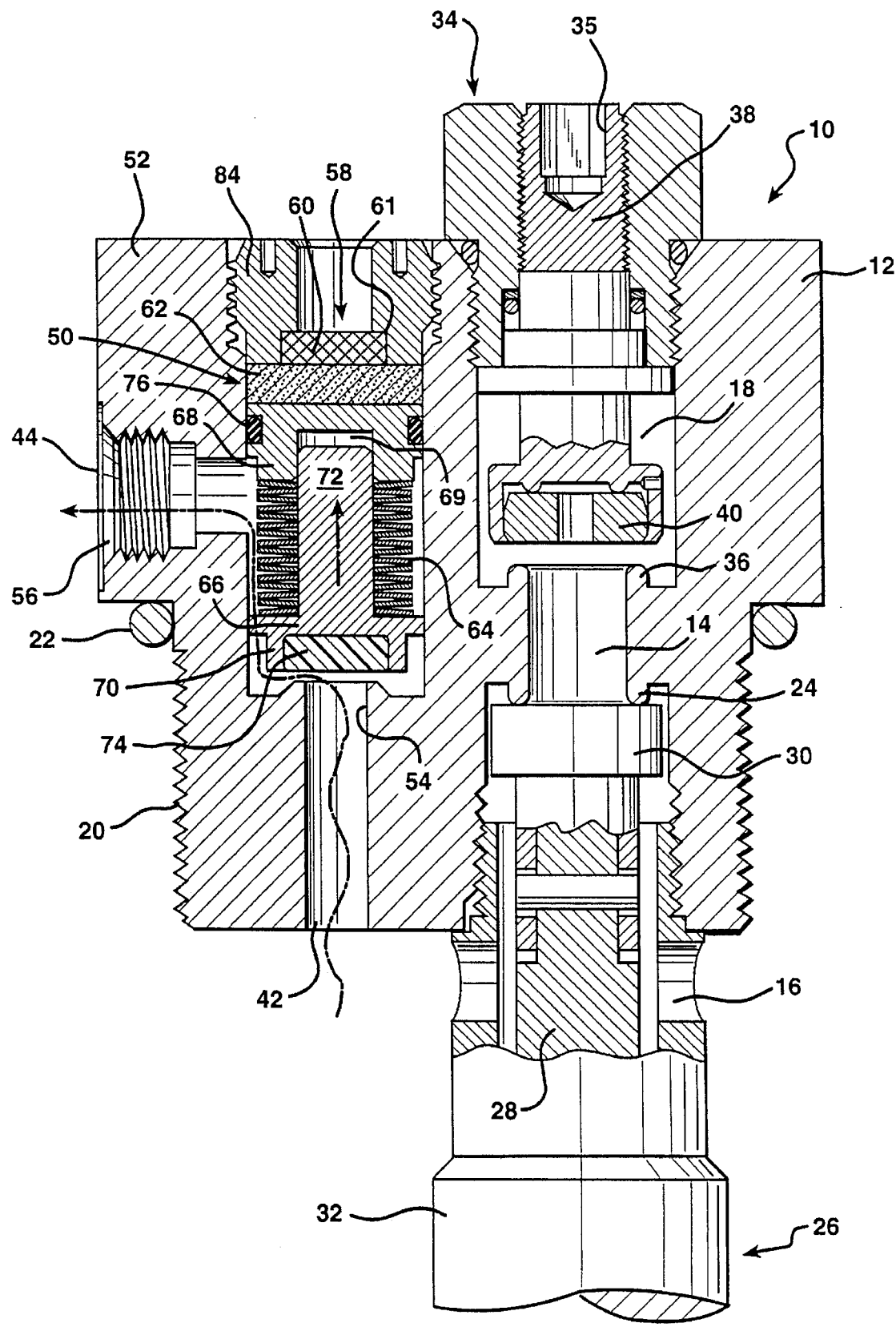
FIG. 4 is a side view, partially in cross-section, of the relief device after a predetermined pressure threshold has been exceeded.

Likewise, if the pressure in the vessel exceeds a predetermined maximum value, such as in the case of overfilling of the vessel or a rise in temperature (but which does not reach the melting temperature of fusible plug 62), relief device 50 will also activate as shown in FIG. 4 (again where like reference numerals depict like elements). As shown in FIG. 4, the pre-set compressive forces exerted by belleville springs 64 will be exceeded by the pressure rise in the vessel. This increased pressure will cause first piston 66 to move upwardly in the direction of the arrow into annular opening 69 of second piston 68, causing gasket 74 to unseat from the inlet 54. Gas will then flow through passage 42 and out port 44 as shown by the arrow. Activation time for relief device 50 is quick. Gas pressure in the vessel will then be reduced until it reaches its predetermined maximum pressure, at which time the compressive forces of the springs will again be sufficient to cause piston 66 and gasket 74 to reseal the inlet. Thus, in this embodiment of the invention, the relief device is reusable.

The compressive forces exerted by springs 64 may be adjusted by turning threaded nut 84 with a suitable tool such as an Allen wrench to tighten or loosen the nut as needed. Nut 84 includes an annular passage therethrough as shown so that melted fusible alloy can escape through fluid escape passage 58.

Figure 2:
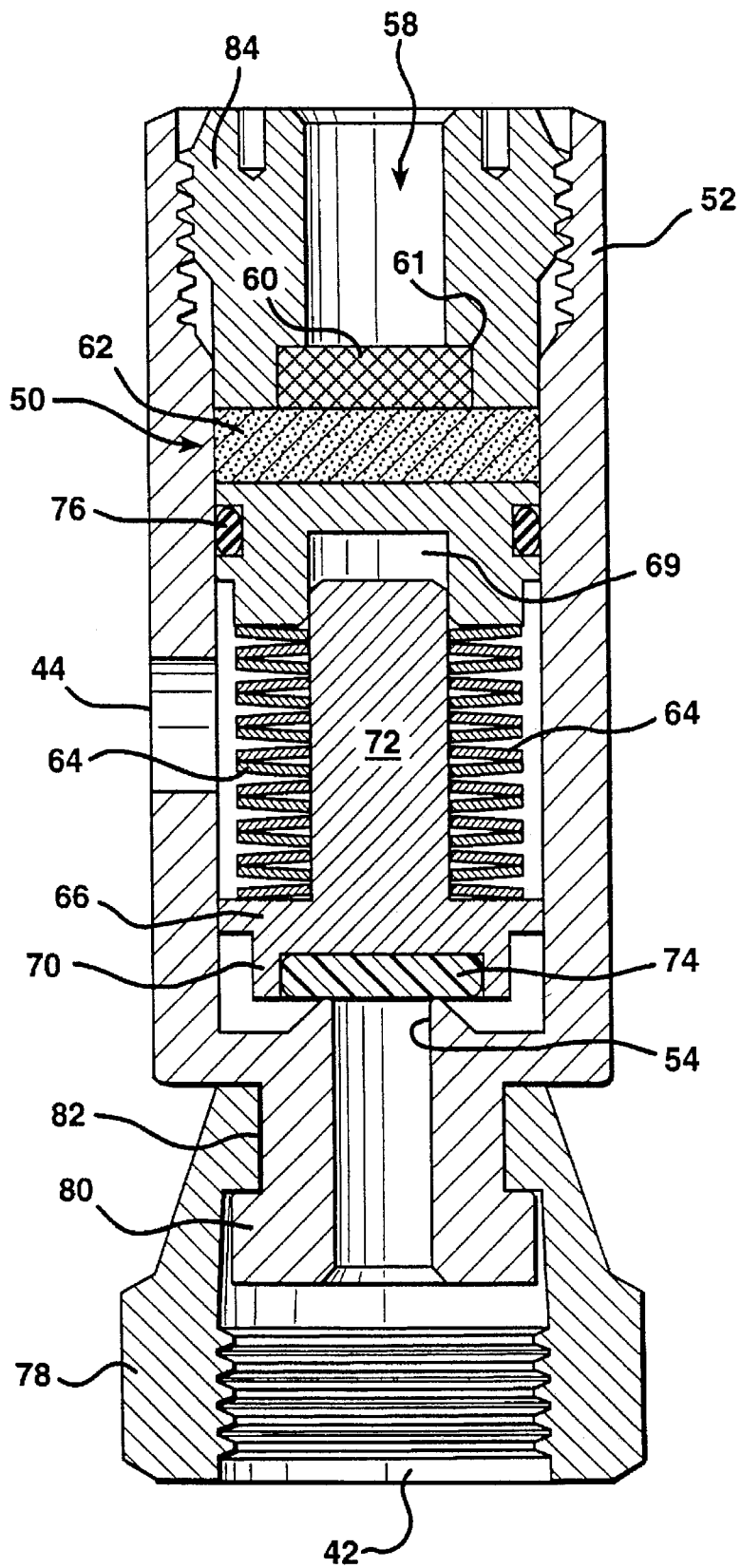
FIG. 2 is a side view, in cross-section, of another embodiment of the invention which has a swivel fitting at the inlet side and which can be adapted to fit any opening in a pressure vessel.
Figure 5:
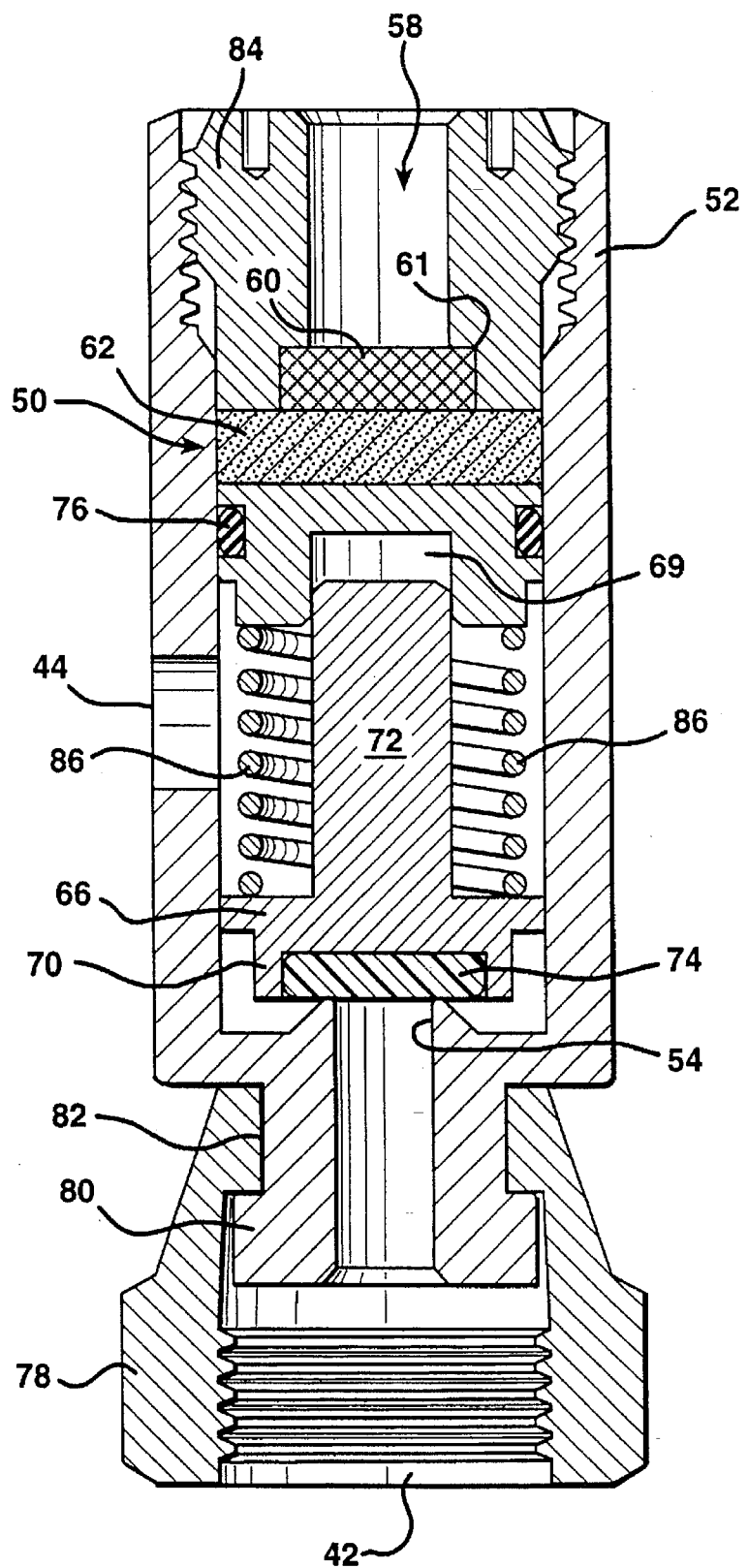
FIG. 5 is a side view, in cross-section, of another embodiment of the relief device of the present invention.

FIG. 2 shows another embodiment of the invention where relief device 50 is a stand alone device and may be externally mounted on essentially any opening in a pressurized vessel through a swivel fitting 78. As shown, body 52 includes a flange portion 80 over which the lip 82 of swivel fitting 78 is fitted. Relief device 50 is then free to rotate a full 360° to provide easy connections, for example, for vent port 44. FIG. 5 shows an alternative embodiment of the relief device in which belleville springs 64 are replaced by a coil spring 86.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A thermally or pressure activated relief device comprising:

a body having an inlet, an outlet, and a fluid flow passage communicating with said inlet and outlet;

said body further including a fluid escape passage having a member therein which is porous to gases and liquids but not to solids;

a plug of a fusible material which melts at a predetermined temperature adjacent to said member;

a first piston positioned in said fluid flow passage, said first piston having first and second ends and being normally biased into a sealing relationship with said inlet; and a second piston positioned in said fluid escape passage, said second piston being normally biased against and applying a compressive force on said plug.

2. A thermally or pressure activated relief device as claimed in claim 1 in which said first and second pistons are biased by one or more belleville springs.

3. A thermally or pressure activated relief device as claimed in claim 1 in which said first and second pistons are biased by a coiled spring.

4. A thermally or pressure activated relief device as claimed in claim 1 in which said first end of said first piston includes a gasket for sealing said inlet.

5. A thermally or pressure activated relief device as claimed in claim 1 in which said second piston includes an annular opening for slidably receiving said second end of said first piston.

6. A thermally or pressure activated relief device as claimed in claim 1 in which said member is comprised of a sintered metal.

7. A thermally or pressure activated relief device as claimed in claim 5 in which said sintered metal is comprised of spheres which have been sintered together.

8. A thermally or pressure activated relief device as claimed in claim 6 in which said sintered metal is bronze.

9. A thermally or pressure activated relief device as claimed in claim 1 in which said plug is not in said fluid flow channel.

10. A thermally or pressure activated relief device as claimed in claim 1 including a swivel fitting over said inlet.

11. A thermally or pressure activated relief device as claimed in claim 1 including a mechanism for adjusting the biasing forces on said first and second pistons.

12. A thermally or pressure activated relief device as claimed in claim 11 in which said adjusting mechanism comprises a threaded nut positioned in said fluid escape passage.

13. A thermally or pressure activated relief device as claimed in claim 12 in which said threaded nut has a flow passage therethrough.

14. A bidirectional valve for controlling the flow of a compressed gas to and from a pressurized vessel comprising:

a) a valve body including a first gas flow passage extending through said valve body and having first and second ends, said first end of said gas flow passage communicating with the interior of said pressurized vessel and said second end of said gas flow passage communicating with an outlet port on said valve body;

b) a valve seat in said flow passage;

c) a solenoid valve including a plunger slidable in said gas flow passage, said plunger including a head for sealing against said valve seat to close said gas flow passage; and d) a second gas flow passage communicating with the interior of said pressurized vessel and a gas vent port on said valve body, and a thermally or pressure activated pressure relief device blocking said second gas flow passage, said pressure relief device comprising a fluid escape passage in said valve body having a member therein which is porous to gases and liquids but not to solids, a plug of a fusible material which melts at a predetermined temperature adjacent to said member, a first piston positioned in said second gas flow passage, said first piston having first and second ends and being normally biased into a sealing relationship with said inlet, and a second piston positioned in said second fluid escape passage, said second piston being normally biased against and applying a compressive force on said plug.

15. A bidirectional valve as claimed in claim 14 further including a second valve seat in said first gas flow passage and a manual lockdown valve positioned in said first gas flow passage between said second valve seat and said outlet port for selectively preventing the flow of gas from said pressurized vessel to said outlet port.

16. A bidirectional valve as claimed in claim 14 in which said first and second pistons in said thermally or pressure activated relief device are biased by one or more belleville springs.

17. A bidirectional valve as claimed in claim 14 in which said first and second pistons in said thermally or pressure activated relief device are biased by a coiled spring.

18. A bidirectional valve as claimed in claim 14 in which said thermally or pressure activated relief device includes a mechanism for adjusting the biasing forces on said first and second pistons.

19. In combination, a pressurized vessel having an opening therein and a thermally or pressure activated relief device mounted in said opening for releasing gas from said pressurized vessel when the temperature adjacent said vessel exceeds a predetermined threshold or when the pressure in the vessel exceeds a predetermined threshold, said thermally or pressure activated relief device comprising:

a body having an inlet, an outlet, and a fluid flow passage communicating with said inlet and outlet;

said body further including a fluid escape passage having a member therein which is porous to gases and liquids but not to solids;

a plug of a fusible material which melts at a predetermined temperature adjacent to said member;

a first piston positioned in said fluid flow passage, said first piston having first and second ends and being normally biased into a sealing relationship with said inlet; and a second piston positioned in said fluid escape passage, said second piston being normally biased against and applying a compressive force on said plug.

20. A pressurized vessel and thermally or pressure activated relief device as claimed in claim 19 in which said first and second pistons are biased by one or more belleville springs.

21. A pressurized vessel and thermally or pressure activated relief device as claimed in claim 19 in which said first and second pistons are biased by a coiled spring.

22. A pressurized vessel and thermally or pressure activated relief device as claimed in claim 19 including a mechanism for adjusting the biasing forces on said first and second pistons.

23. A pressurized vessel and thermally or pressure activated relief device as claimed in claim 22 in which said adjusting mechanism comprises a threaded nut positioned in said fluid escape passage.

24. A pressurized vessel and thermally or pressure activated relief device as claimed in claim 23 in which said threaded nut has a flow passage therethrough.

* * * * *